US009782098B2

(12) United States Patent
Chou

(10) Patent No.: US 9,782,098 B2
(45) Date of Patent: Oct. 10, 2017

(54) CARDIOVASCULAR MONITORING DEVICE

(71) Applicant: Chang-An Chou, Taipei (TW)

(72) Inventor: Chang-An Chou, Taipei (TW)

(73) Assignee: MD Biomedical, Inc., Taipei (TW)

(*) Notice: Subject to any disclaimer, the term of this patent is extended or adjusted under 35 U.S.C. 154(b) by 130 days.

(21) Appl. No.: 14/623,525

(22) Filed: Feb. 17, 2015

(65) Prior Publication Data

US 2016/0235325 A1 Aug. 18, 2016

(51) Int. Cl.
*A61B 5/0408* (2006.01)
*A61B 5/022* (2006.01)
*A61B 5/044* (2006.01)
*A61B 5/0245* (2006.01)
*A61B 5/021* (2006.01)
*A61B 5/024* (2006.01)
*A61B 5/0404* (2006.01)
*A61B 5/0452* (2006.01)
*A61B 5/00* (2006.01)

(52) U.S. Cl.
CPC ........ *A61B 5/04085* (2013.01); *A61B 5/0245* (2013.01); *A61B 5/02141* (2013.01); *A61B 5/02225* (2013.01); *A61B 5/02233* (2013.01); *A61B 5/02241* (2013.01); *A61B 5/02438* (2013.01); *A61B 5/0404* (2013.01); *A61B 5/044* (2013.01); *A61B 5/0452* (2013.01); *A61B 5/681* (2013.01); *A61B 5/6825* (2013.01); *A61B 5/6826* (2013.01); *A61B 5/022* (2013.01); *A61B 2562/0247* (2013.01)

(58) Field of Classification Search
CPC ............ A61B 5/04085; A61B 5/02233; A61B 5/0245
USPC ........................................ 600/384, 390, 490
See application file for complete search history.

(56) References Cited

U.S. PATENT DOCUMENTS

| | | | |
|---|---|---|---|
| 8,086,301 B2* | 12/2011 | Cho | A61B 5/021 600/513 |
| 8,795,185 B2* | 8/2014 | Cho | A61B 5/0059 600/480 |
| 2007/0100247 A1* | 5/2007 | Platt | A61B 5/02233 600/513 |

* cited by examiner

Primary Examiner — Lee S Cohen

(57) ABSTRACT

The present invention is related to a cardiovascular monitoring device including an inflatable cuff for surrounding a limb of a user, at least a first and a second electrodes, a controlling circuitry with a processor accommodated in a housing, and a display element. The controlling circuitry is configured to perform a blood pressure measurement through controlling a pressure inside the inflatable cuff, and perform an electrocardiogram measurement by using the electrodes. The processor is also configured to provide a diastolic blood pressure and a systolic blood pressure when the blood pressure measurement is performed, and to provide a heart rhythm information when the electrocardiogram measurement is performed. Further, for achieving a better and more stable contact between the electrodes and the user's skin, the present invention provides an improved structure with electrodes arranged thereon based on the conventional blood pressure monitor.

2 Claims, 9 Drawing Sheets

CARDIOVASCULAR MONITORING DEVICE

RELATED APPLICATIONS

The present invention is a continuation-in-part of U.S. patent application Ser. No. 13/558,339, filed on Jul. 26, 2012, titled "CARDIOVASCULAR MONITORING DEVICE", which is abandoned and incorporated herein by reference.

FIELD OF THE INVENTION

The present invention relates to a cardiovascular monitoring device with both functions of blood pressure and electrocardiogram measurements, and more particularly to a cardiovascular monitoring device which provides an improved contact stability between the user's skin and the electrocardiogram electrode mounted thereon.

BACKGROUND OF THE INVENTION

Modern people pay more and more attention on their cardiovascular health. Blood pressure monitor is one of the most common home-use devices for daily monitoring of cardiovascular health. Not only it is convenient to use, but also the high blood pressure is one of the risk factors related to many kinds of chronic diseases, such as, heart diseases, and diabetes.

Recently, owing to users' demands and also the technical development, the function of the blood pressure monitor has been improved a lot. In addition to the blood pressure, the blood pressure monitor now can provide more information related to the cardiovascular system, e.g., the average heart rate and the indication of irregular heartbeat. However, the function of irregular heartbeat detection provided by the blood pressure monitor should only be a referential indication for heart rhythm because it is provided based on the arterial pulses detected.

Arrhythmia is one common kind of heart rhythm problem whose symptom is the rate or rhythm of the heartbeat is too fast, too slow, or with an irregular rhythm. Some arrhythmias are life-threatening medical emergencies that can result in cardiac arrest. Others cause symptoms such as an abnormal awareness of heart beat (palpitations), and may be merely uncomfortable. Except of congenital and some heart diseases, some medical conditions such as diabetes and high blood pressure, and stress, caffeine, smoking, alcohol etc. can also affect the heart's natural beating pattern and lead to arrhythmia. Thus, arrhythmia really is a symptom that related to not only heart itself but also the cardiovascular system and physical condition, and should pay more attention to. Up to now, the most accurate way to diagnose arrhythmia is ECG test.

According to the descriptions above, in addition to the blood pressure, it will be better to also consider the electrocardiogram as discussing the cardiovascular health. Therefore, if there can have a device simultaneously provide these two functions, blood pressure measurement and electrocardiogram measurement, it will be a significant improvement for cardiovascular monitoring. This will be very helpful in collecting these two most important data for doctor's diagnosis and also in long-term tracking of cardiovascular health.

For combining the electrodes on the conventional blood pressure monitor, one thing must be considered is what type of electrode should be used. Because it is a home-use device, the used electrode should be able to provide the user an easy, simple and convenient way to perform the electrocardiogram measurement. Therefore, the electrode which can achieve the measurement without using the conductive gel and at the same time can be mounted on the surface of the monitor will be a better choice. Besides, adopting this type of electrode will also facilitate the utilization to the original structure of the blood pressure monitor. Accordingly, the following issue will be how the electrodes is placed on the blood pressure monitor since, without the conductive gel, the contact stability between the user's skin and electrode which is related to the accuracy of measurement results becomes even more critical. As known, there are some situations might influence the acquired ECG signals, for example, the contacted area of the electrode, which portion of skin is employed to perform the measurement, and the posture of the user to contact the electrodes, and one of the most common sources of noises is the excessive muscle tension which is related to the user's posture during the measurement. Therefore, how to improve the structure and the electrodes arranged thereon to minimize the possible influences described above becomes an important issue.

Consequently, the object of the present invention is to provide a cardiovascular monitoring device which utilizes the structure of the conventional blood pressure monitor to position the electrode in an ergonomic way.

Another object of the present invention is to provide a cardiovascular monitoring device in which the positions of electrodes are designed to achieve a stable contact with the user's skin.

SUMMARY OF THE INVENTION

The present invention is related to a cardiovascular monitoring device including an inflatable cuff, for surrounding a limb of a user, at least a first and a second electrodes, a controlling circuitry with a processor accommodated in a housing, and a display element, wherein one of the electrodes is implemented as dry electrode. The controlling circuitry is configured to perform a blood pressure measurement through controlling a pressure inside the inflatable cuff, and perform an electrocardiogram measurement by using the electrodes. The processor is also configured to provide a diastolic blood pressure and a systolic blood pressure when the blood pressure measurement is performed, and to provide a heart rhythm information when the electrocardiogram measurement is performed. The display element is used for showing the diastolic and systolic blood pressures and the heart rhythm information.

Preferably, the heart rhythm information can include, but not limited, an average heart rate and/or an indication of arrhythmia, and other information about heart rhythm that can be derived from the acquired electrocardiogram. And, other than the blood pressure and the heart rhythm information, the processor can further configured to provide at least one of ST value, QRS, PR, QTc and parameters related to HRV when the electrocardiogram measurement is activated.

Further, for achieving a better and more stable contact between the electrodes and the user's skin, the present invention provides an improved structure with the electrodes arranged thereon based on the conventional blood pressure monitor.

In an aspect of the present invention, a holding structure is provided to mount the first electrode thereon, so that the user can complete the contact simply by holding the structure. And, the holding structure is formed to have an ergonomic shape for further ensuring the contact stability between the first electrode and the holding hand. For example, the shape of the holding structure can be formed to have an arc surface conforming to the bending of the holding hand, and/or the position of the first electrode can be located at where the holding hand can easily contact. Here, the holding structure can be implemented as a structure extended from the housing or the cuff, or be integrated with the housing. And, the shape of the holding structure can be carried out in accordance with different demands, such as, to be a long or ball-like shape, or any other shape that is convenient to hold.

Particularly, the second electrode also can be mounted on the holding structure, so that the user can contact the first electrode by holding and move the holding structure to contact the second electrode with another portion of the skin, such as, another limb (e.g., the leg or another hand), or the chest, so as to achieve the electrocardiogram measurement in a convenient way.

In another aspect of the present invention, the first and the second electrodes are arranged on opposite contactable surfaces of a portion of the device, e.g., the housing and/or the cuff, so that when a force is applied on one of the electrodes, both electrodes can be contacted with different portions of skin at the same time. Therefore, when the device is arranged on the user, e.g., through the cuff surrounds the limb, the contacts of all electrodes can be completed simultaneously as one hand applies a force on one of the electrodes. Alternatively, the pressing also can be achieved by the user moves the surrounded hand to contact the electrode with the chest. Thus, there is no limitation.

Particularly, a force-receiving structure extended from the housing or the cuff for carrying the first and the second electrodes respectively on the opposite surfaces thereof can be further provided, so that the user can have a more recognizable area to press.

In still another aspect of the present invention, an elastic structure is provided to ensure that the first electrode can have a stable contact with the skin when the cardiovascular monitoring device is arranged on the user. Here, depending on the position of the first electrode, on the housing or on the cuff, the elastic structure can be implemented into different ways. For example, if the first electrode is mounted on the housing, the elastic structure can be a clamp integrated with the housing with the first electrode mounted inside, so that when the housing is clamped on the user's finger, palm, or limb, the contact can stably achieved at the same time. Alternatively, if the first electrode is mounted on the cuff, the elastic structure can be implemented to be a clamp or an elastic band integrated with the cuff, so that the contact instability or noises caused from the inflation can be avoided. Particularly, the elastic structure also can be integrated with the electrode itself, namely, the electrode is formed to directly own the flexibility for remaining the contact with the skin, such as a clamp-type electrode. Therefore, there is no limitation.

Particularly, when the electrode is mounted on the cuff, for further stabilizing the contact, it can be implemented to control the timing for performing the electrocardiogram measurement based on the inflation of the cuff. For example, by employing a program, the electrocardiogram measurement can be restricted to perform only when the inflation is steady or paused, namely, when the variation is stopped, so as to maximize the contact stability.

It should be noted that the embodiments described above are not restricted to use alone, and different embodiments can be combined or integrated to achieve the purpose of providing stable electrode contact. And, although the descriptions are focused on the first electrode for simplicity, the second electrode and other electrodes also can employ the embodiment described above without limitation.

Here, the surface wherein the electrode described here is mounted on can be any contactable surface of the cardiovascular monitoring device, namely, any contactable surface of the housing, the cuff, and/or the extending structure. In a particular embodiment, the contactable surface can be implemented to be an inner surface of a structure for receiving or accommodating the finger(s) and/or the hand, such as, the inner surface of a hole mounted on the housing or the cuff, or the inner surface of a finger cot or a glove (the extending structure) extended from the housing or the cuff. Besides, the receiving or accommodating structure also can employ an elastic structure inside to restrain the movement of the finger(s) or the hand, so as to further reduce the noises caused thereby.

Particularly, if it is implemented to be the finger cot or glove, the second electrode also can be mounted on the outer surface thereof, so that the user can achieve the contact with the second electrode by moving the covered hand or finger to contact/hold another limb or the chest, or by using another hand to hold the covered hand or finger, without limitation.

Preferably, the cardiovascular monitoring device can further include a memory for storing the acquired blood pressure and electrocardiogram signals and related information for further downloading. Moreover, the cardiovascular monitoring device also can be implemented to connect with an additional electrode or sensor, e.g., an oximeter or a reference electrode, for further improving the measurement result and/or expand the function. Besides, at least one of the electrodes can be connected with a pressure detecting element, a touch sensing element, or a switch for sensing the contact applied thereon, so as to inform the user that if the applied force is high enough.

Accordingly, through employing an improved structure design with electrode arranged thereon based on the conventional structure of blood pressure monitor, the present invention provides a cardiovascular monitoring device having both functions of blood pressure and electrocardiogram measurements with easier, simpler and more convenient electrode contact manner. And, through the ergonomic design, the stability of contact between the electrode and the skin can be further improved for providing a more accurate result.

BRIEF DESCRIPTION OF THE DRAWINGS

A more detailed understanding of the invention may be had from the following descriptions of preferred embodiments, given by way of example, and to be understood in conjunction with the accompanying drawings, wherein.

DESCRIPTION OF THE PREFERRED EMBODIMENTS

The present invention is related to a cardiovascular monitoring device with both functions of blood pressure measurement and electrocardiogram measurement, so that through operating one single device, multiple kinds of important information related to cardiovascular health can be obtained.

For integrating two kinds of measurements, the present invention adopts the basic structure of the blood pressure monitor to position the ECG electrodes thereon, and more particularly, the present invention also provides a design which facilitates an easy and ergonomic operation for the user and ensures a stable contact between the electrodes and the user's skin, so as to significantly reduce the influence of excessive muscle tension. Therefore, it should be noted that the present invention can be applied to all kinds of blood pressure monitors, such as, the wrist blood pressure monitor and the upper-arm blood pressure monitor, without limitation.

Figure 1:
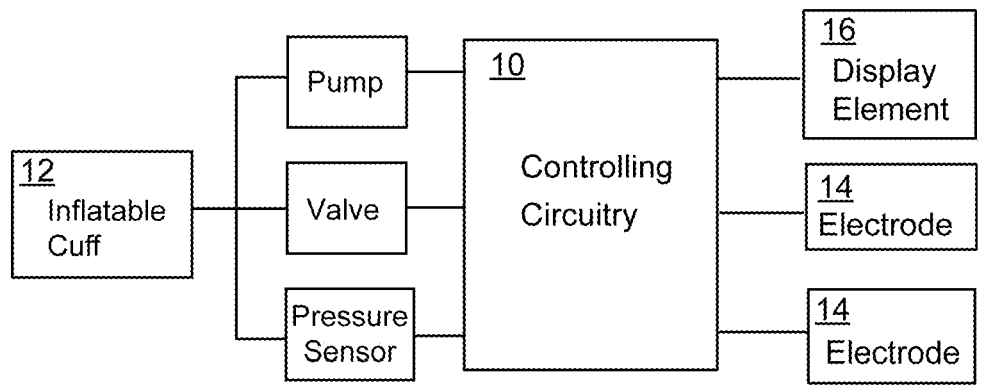
FIG. 1 shows a circuit diagram of a cardiovascular monitoring device according to the present invention.
Figure 2:
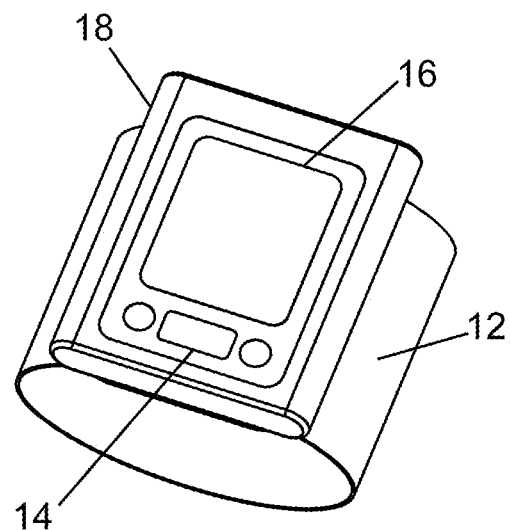
FIG. 2 is a schematic view showing the cardiovascular monitoring device according to the present invention.
Figure 5A:
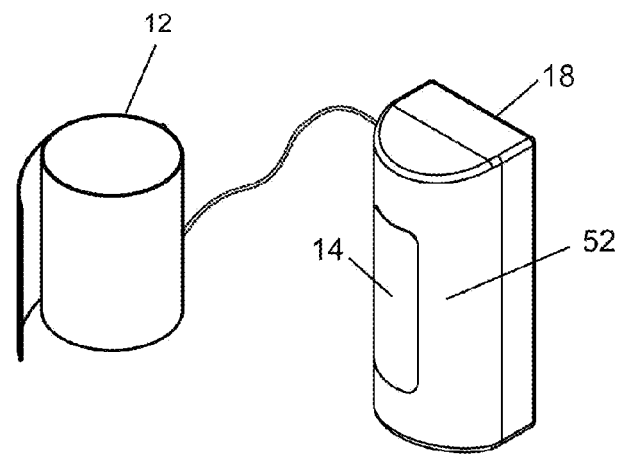
FIGS. 5A-5C are schematic views showing exemplary embodiments of the cardiovascular monitoring device in an another aspect of the present invention.
Figure 5B:
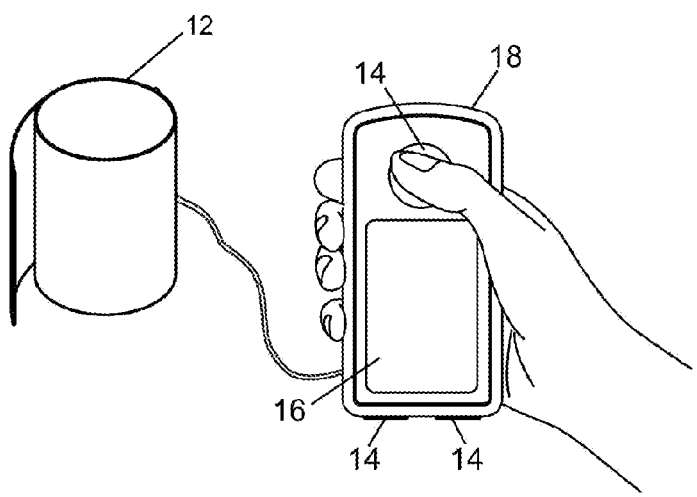
Figure 5C:
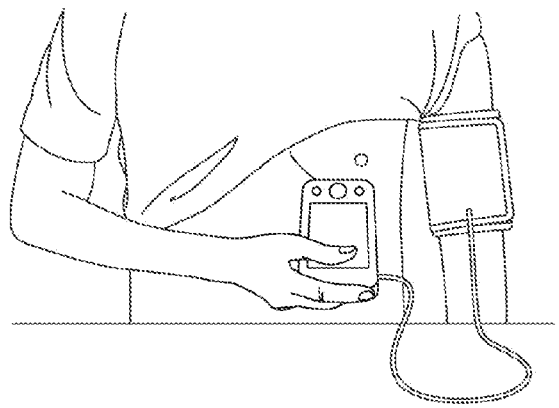

Please refer to FIG. 1 which is a schematic view showing a cardiovascular monitoring device according to the present invention. As shown, the cardiovascular monitoring device includes a controlling circuitry 10, an inflatable cuff 12, a pump, a valve, a pressure sensor, at least two electrodes 14, and a display element 16. Here, the controlling circuitry 10 is implemented to perform the blood pressure measurement and the electrocardiogram measurement via the connected cuff 12 and the electrodes 14. Therefore, the controlling circuitry 10 can include, but not limited, some common electronic components for achieving the measurements, for example, a processor, at least an AD converter(s), an amplifier, a filter etc., which are all well known by ones skilled in the arts and thus are omitted in the description. Then, as shown in FIG. 2, a housing 18 carried by the cuff 12 can be further provided for accommodating the controlling circuitry therein and having the display element 16 and an operation interface mounted thereon. Another way is the housing is connected with the cuff via an air tube, as shown in FIGS. 5A-5C.

Moreover, the device can further includes a memory for the storage of signals, analysis results and/or related information, and more preferably, the memory can be implemented to be removable. For outputting the stored data, the removable memory is a convenient choice, for example, the user can bring the removable memory with the measurement/analysis results stored therein to the doctor. In addition to using the removable memory, the stored data also can be outputted to an outer device (e.g., a computer) through a wired connection (e.g., via at least a transmission port, such as, USB port) or a wireless communication, e.g., Bluetooth.

In the present invention, because both the blood pressure and the electrocardiogram are measured, the preloaded program in the processor can further include algorithms related to electrocardiogram, except the ones in the conventional blood pressure monitor. The algorithms can be divided into three groups. One is related to blood pressure measurement, for example, but not limited, diastolic blood pressure, systolic blood pressure and heart rate. One is related to electrocardiogram measurement, for example, but not limited, heart rate, arrhythmia, ST value, QRS, PR, QTc, and parameters related to HRV (Heart Rate Variability) including time domain statistical parameters, e.g., SDNN, RMSSD, NN50, and pNN50, time domain geometrical parameters, e.g., RR triangular index, and TINN, and frequency domain parameters, e.g., LF, HF, and LF/HF. The other is related to both, for example, but not limited, artifact removal and PTT (Pulse Transit Time, which is the time it takes the pulse pressure waveform to propagate through a length of the arterial tree).

The most difference from the conventional blood pressure monitor is the device of the present invention can provide the information that must come from the electrocardiogram, such as the information about heart rhythm, e.g., the average heart rate, and the indication of arrhythmia, and other information judged from the waveform of electrocardiogram, e.g., ST values which are related to myocardial infarction.

Therefore, the user not only can obtain more kinds of analysis results but also in some level can have more accurate results, e.g., comparing the indication of irregular heartbeat with the indication of arrhythmia. Besides, because the blood pressure and the electrocardiogram are actually relative to each other, two kinds of signals can have a cross reference for obtaining the information representing other physiological conditions, such as, pulse transit time. Further, the comparison between the arterial pulses and ECGs also is helpful to remove the artifact.

And, because the present invention directly measures the electrocardiogram, it also provides the possibility to obtain the information related to the heart condition directly from the electrocardiogram, so that compared with the conventional blood pressure monitor, the present invention provides not only more operation options but also more information related to cardiovascular health.

In the present invention, the measurement of electrocardiogram is achieved by contacting the electrodes with different portions of user's skin. The most convenient way for the user is to implement the electrode as dry electrode mounted on the surface of the device. When the dry electrode is employed, for achieving the electrocardiogram measurement, the user can directly contact the electrode without the medium, e.g., the conductive gel, so the measurement can be performed at any time. And, because the dry electrode is uneasily destroyed and can be easily maintained, the inconvenience of replacing the electrode is also avoided. Here, it can be both or only one of the electrodes to be implemented as the dry electrode(s) without limitation. Alternatively, another option is the patch electrode, for example, a reusable patch electrode or a replaceable patch electrode mounted on the surface of the device which also can be used without the conductive gel. Therefore, there is no limitation.

ECG electrodes of the present invention can be mounted on the surface available from the whole device, e.g., the surface of the housing, the surface of the cuff, or the surface of an extended structure, namely, anywhere can be contacted with the user's skin. Since the electrocardiogram measurement should be relied on the contact between the electrodes and the skin, the design of the present invention is mainly to provide maximum contact stability and minimum operation steps without significantly changing the conventional structure of the blood pressure monitor, so as to reduce the manufacturing cost. In addition, because the inflation of the cuff might influence the contact stability if the electrode is mounted on the cuff, the present invention also hopes to overcome this problem.

In accordance with the present invention, for ensuring the contact stability of the electrodes, two kinds of approaches are employed, one is to rely on a force application from the user and the other is to let the electrode itself to apply force on the user's skin.

In a first aspect, the whole device with the electrodes thereon is designed to provide a natural and convenient way for the user to contact the electrodes, so as to ensure a stable force application from the user.

Figure 3A:
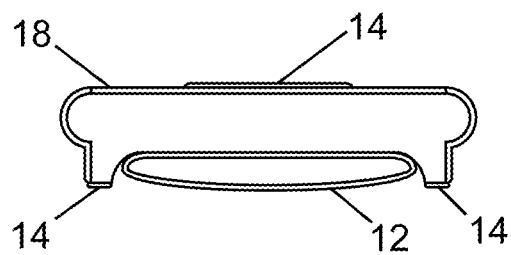
FIGS. 3A-3B are sectional views showing exemplary embodiments of the cardiovascular monitoring device in an aspect of the present invention.
Figure 3B:
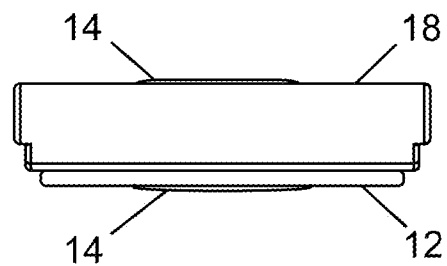

In a preferred embodiment, the ECG electrodes are configured to simultaneously contact different portions of user's skin when the user applies a force on one of electrodes. Thus, in this case, the housing should be carried by the cuff. Please refer to FIG. 3A and FIG. 3B, ECG electrodes 14 are respectively mounted on the surfaces of the housing 18 and/or the cuff 12, and particularly, multiple electrodes 14 are mounted on opposite surfaces. Therefore, when the force is applied on one of the electrodes, the remainder electrode(s) can therefore also be pressed by the same force. As shown in FIG. 3A, the electrodes are positioned at opposite surfaces of the housing 18 and due to the rigidity of the housing 18, the electrodes which are not directly opposite to each other also can contact with the user's skin at the same time through only one force application. Further, FIG. 3B provides another embodiment in which the electrodes 14 are located on the housing 18 and the cuff 12 and opposite to each other.

Figure 4A:
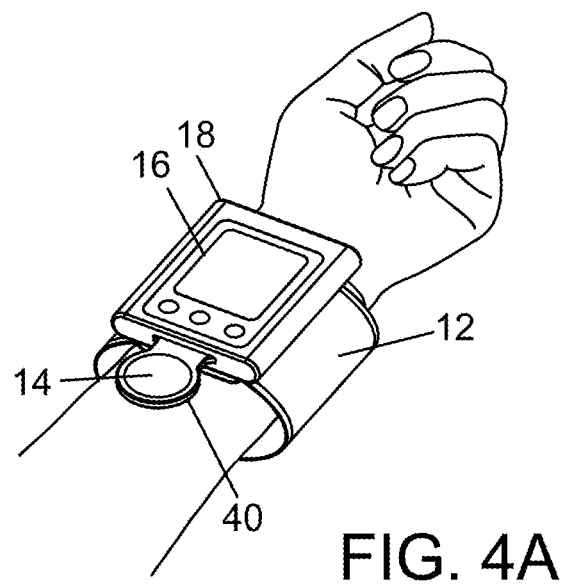
FIGS. 4A-4B are schematic views showing further exemplary embodiments of the cardiovascular monitoring device in an aspect of the present invention.
Figure 4B:
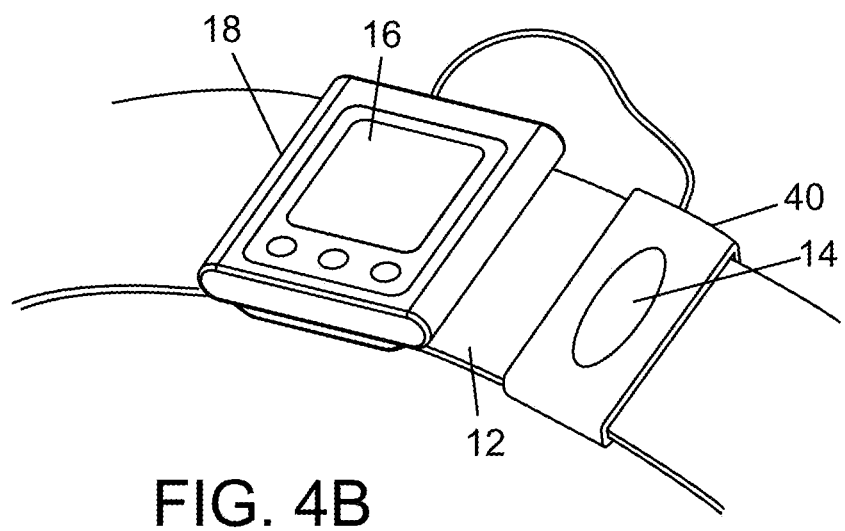

Except directly mounting the electrodes on the housing and/or the cuff, it is also preferable to have the electrodes mounted on opposite surfaces of a force-receiving structure 40 extended from the housing/cuff. For example, as shown in FIG. 4A, the force-receiving structure 40 can be a large-area and recognizable region for providing user a more convenient operation. Alternatively, as shown in FIG. 4B, the force-receiving structure 40 with the electrodes 14 on the opposite surfaces thereof also can be formed to surround the cuff and be capable of moving along the cuff, so as to be ergonomic.

This opposite mounting manner of electrodes according to the present invention also makes a more convenient operation possible. That is, the user can move the hand surrounded by the cuff to contact the electrode on the housing or on the outer surface of the cuff directly with the chest, and under this situation, not only the opposite electrodes can contact the surrounded hand and the chest at the same time, but the measurement through contacting the chest also can bring out clearer signals. And, more preferably, this measurement method conforms to one of the standard poses for using the wrist-type blood pressure monitor.

In another preferred embodiment, the arrangement of electrodes also can be implemented that at least one electrode is contacted by a holding hand, so that, in this case, the housing is separated from the cuff. For example, the electrode can be mounted on the housing 18 directly or on a holding structure extended from the housing or the cuff for being held by the user. Here, the shape of the held housing/holding structure and the position/shape of the electrode thereon are not limited but conforming to the holding ergonomics and being able to achieve a natural and convenient operation. For example, as shown in FIG. 5A, the housing/holding structure can be formed to have an arc surface 52 for conforming to the bending of fingers to provide an easier and relaxer holding posture to contact the electrode 14 and thus reducing the excessive muscle tension. Here, the structure also can be formed to have a column or ball-like shape depending on the real demands. Alternatively, as shown in FIG. 5B, the electrode on the housing/holding structure can be designed to locate at a position where the relaxed thumb can be contacted. Here, preferably, the electrode can be formed into a button-like shape for providing an intuitive contact operation, and even more preferably, the button can be further implemented as the button for triggering the measurement so as to simplify the operation procedure. Besides, it also can be that the electrode(s) is(are) located at the position(s) where can be contacted by the other four fingers in an easy and relax way. Alternatively, as shown in FIG. 5C, the electrodes also can be mounted on the opposite surfaces of the housing, so as to provide another holding manner. Thus, there is no limitation.

Here, particularly, except the electrode(s) contacted by the holding hand, other electrode(s) also can be mounted on the surface of the housing/holding structure, as shown in FIG. 5B. While the user uses one hand to hold the housing/holding structure and contact the electrode(s) thereon, other electrode(s) can contact other portions of the user, such as, another limb (e.g., the leg or another hand) or the chest, as shown in FIG. 5C, so as to achieve a simultaneous contact of electrodes.

Furthermore, in a second aspect of the present invention, the whole device with the electrodes thereon is designed to allow the electrode itself to produce a force for achieving a stable contact with the user's skin.

Figure 6A:
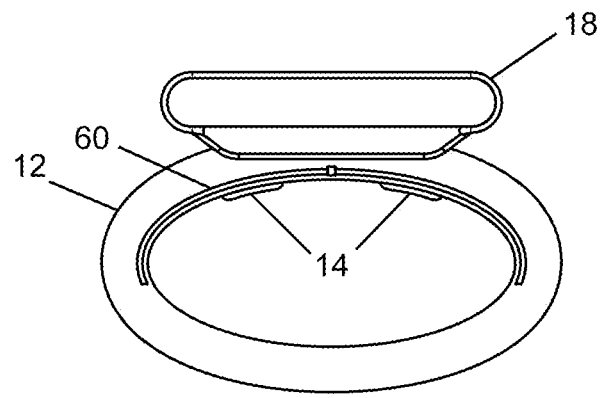
FIG. 6A is a sectional view showing an exemplary embodiment of the cardiovascular monitoring device in still another aspect of the present invention.
Figure 6B:
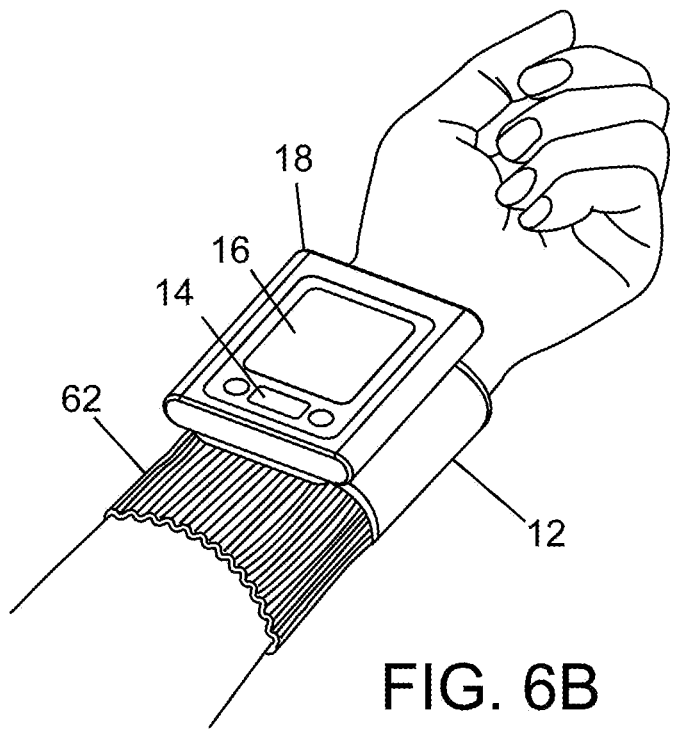
FIGS. 6B-6D are schematic views showing other exemplary embodiments of the cardiovascular monitoring device in still another aspect of the present invention.
Figure 6C:
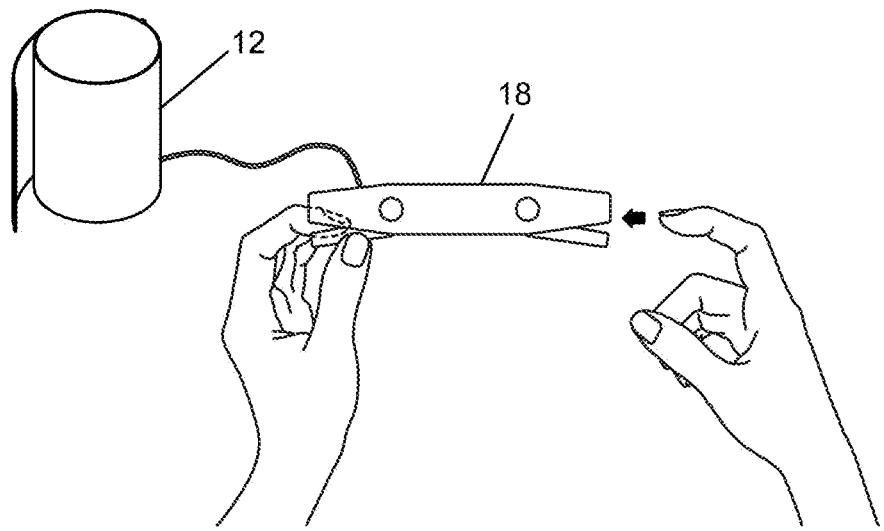
Figure 6D:
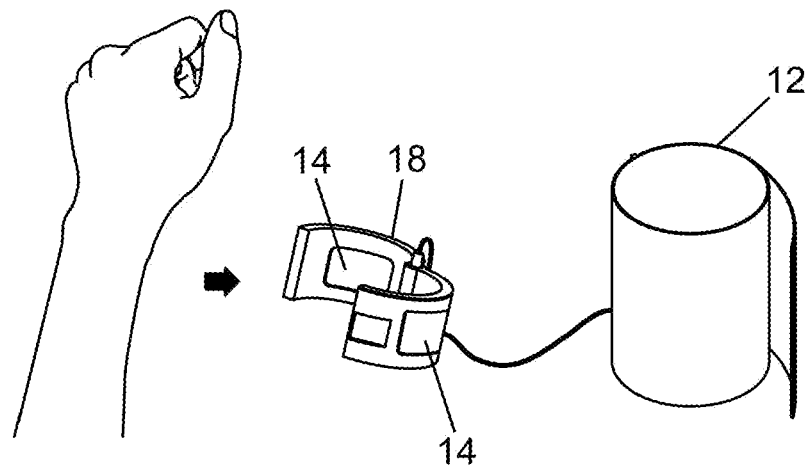

In a preferred embodiment, an elastic structure is employed to ensure the electrode contact. The elastic structure can be integrated with the housing, the cuff or even the electrode itself. For example, if the electrode 14 is mounted on the cuff 12, the elastic structure can be implemented to be an elastic clamp 60 (FIG. 6A) integrated with the cuff and near the electrode, or an elastic band 62 (FIG. 6B) formed at the edges of the cuff and will not be inflated, for forcing the electrode to contact the skin. Alternatively, if the electrode is positioned on the housing 18, the elastic structure can be integrated with the housing, as shown in FIG. 6C and FIG. 6D, so that the housing 18 can clamp a portion of the limb or the hand and thus to force the electrode inside to contact the skin. More particularly, the elastic structure also can be implemented to integrate with the electrode itself, that is, the electrode itself can be formed to be flexible, for example, a clap type electrode for directly applying force on the skin. Therefore, there is no limitation to the type, shape and position of the elastic structure and it can be varied according to the real situation.

Moreover, particularly, when the electrode is mounted on the inflatable cuff, for further ensuring the contact stability, it also can restrict the inflation of the cuff during the ECG measurement. For example, through a program control, ECG measurement can be set to perform as the inflation pressure is steady or is paused (that is, the inflation does not have variation), such as, before the inflation, when the inflation remains unchanged, or when the inflation is completed. Alternatively, it also can be implemented that the ECG measurement is performed only when the inflation achieves a preset threshold (that is, when the contact force is high enough). Therefore, the instability caused by the inflation can be further avoided.

It should be noted that the embodiments described above are not restricted to be used alone, and different embodiments can be integrated or combined to provide further stability and convenience for electrode contact and operation procedure. For example, as shown in FIG. 6D, owing to the structure of the housing 18, not only the inner electrode can be contacted through the elastic structure, but the electrode on the outer surface can be contacted by the holding operation. And, although the descriptions are focused on the first electrode for simplicity, the second electrode and other electrodes also can employ the embodiment described above without limitation.

Figure 7A:
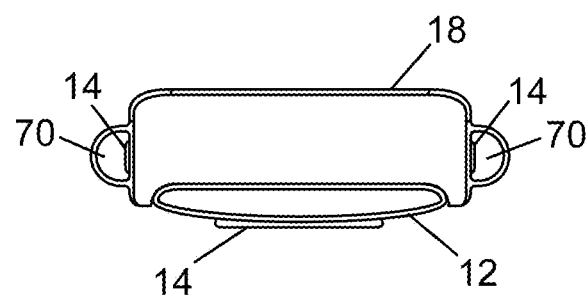
FIGS. 7A-7B are sectional views showing examples of the cardiovascular monitoring device according to the present invention.
Figure 7B:
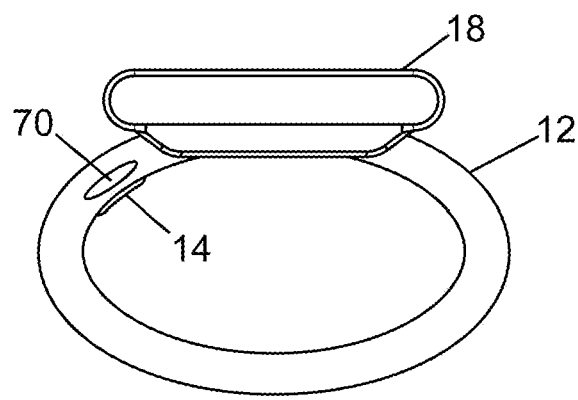
Figure 7C:
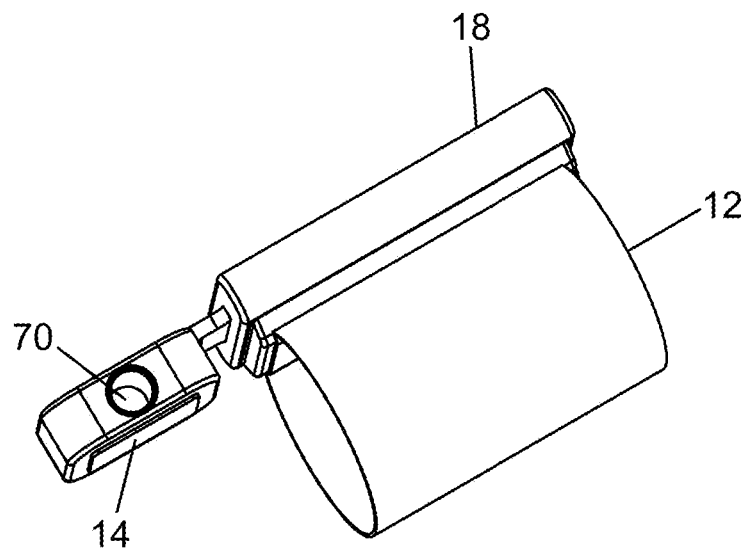
FIGS. 7C-7F are schematic views showing other examples of the cardiovascular monitoring device according to the present invention.
Figure 7D:
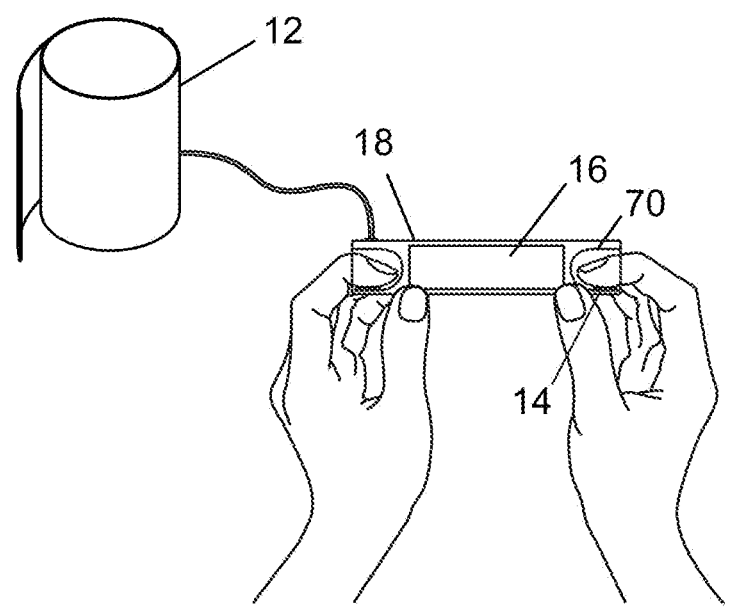
Figure 7E:
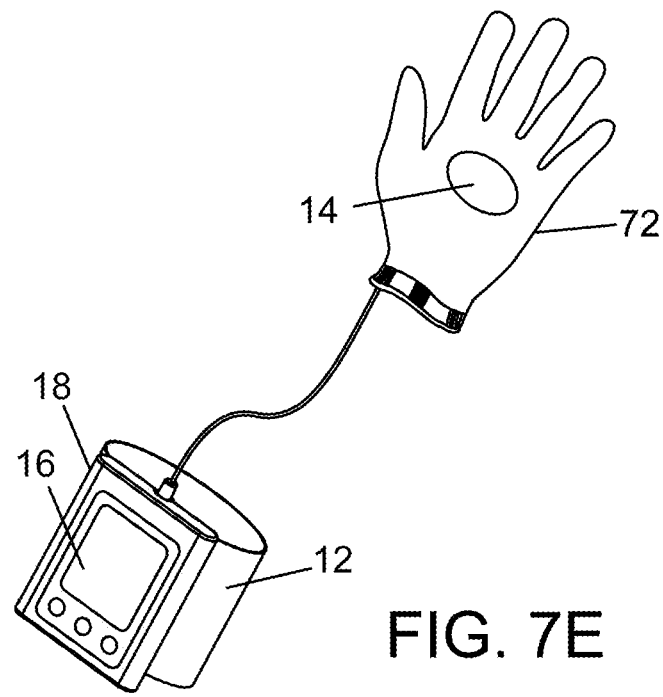
Figure 7F:
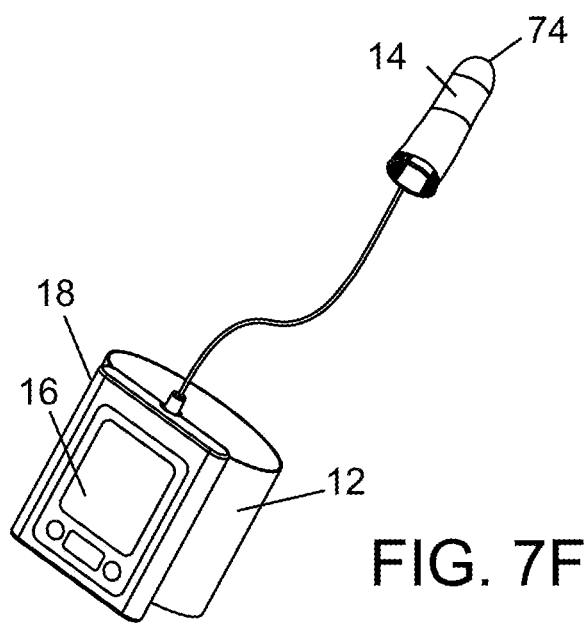

FIGS. 7A~7E are some other examples. As shown, the surface(s) for mounting the electrode(s) can be one or more indentations formed on the housing/cuff/extended structure. In FIG. 7A, the housing is formed to have two indentations 70 respectively having an electrode 14 positioned on the inner surface thereof for receiving the finger, so that when the fingers are inserted into the indentations 70, the contact with the electrodes 14 can be done at the same time. Then, through the fingers press down, the electrode on the opposite surface can contact another portion's skin. In FIG. 7B, the indentation 70 is formed in the cuff 12. And, similarly, the inserted finger can contact the electrode inside and press down to force the other electrode to contact with the another portion's skin. In FIG. 7C, the indentation 70 is formed in the extended structure and another electrode is located under the structure. In FIG. 7D, the electrodes are respectively mounted in different indentations of the housing for contacting the inserted fingers. Here, more particularly, the indentation (in the housing, cuff or extended structure) can further employ the elastic structure inside to ensure the contact between the electrode(s) and the finger. Furthermore, FIGS. 7E and 7F illustrate another kind of examples. The indentation is implemented as an elastic glove 72 or an elastic finger cot 74 with the electrodes mounted on the inner and outer sides thereof. Therefore, for completing the contacts of all electrodes, the hand or finger cover by the glove 72 or the finger cot 74 can be held by another hand, can hold another limb or hand, or can contact another limb, hand or chest.

Moreover, two or more electrodes also can be implemented in different ways. For example, one electrode can be positioned in the elastic structure of the housing and the other two can be mounted on the opposite sides of the extended structure. Alternatively, it also can be one electrode is positioned on the elastic structure of the cuff and the other is mounted on the housing to be held. Therefore, depending on the real situation and demand, the implementation can be varied without limitation. And, owing to the device structure and the electrode arrangement of the present invention, the way to achieve the contacts of more than two electrodes at the same time can have more choices.

Besides, in the present invention, for facilitating the electrocardiogram measurement, the electrodes, especially the dry electrode(s), (partial or all) can be connected to a sensor for detecting and notifying the user if the contact on the electrode is proper. For example, a pressure detecting element can be used to detect the applied force on the electrode, e.g., a pressure sensor, or a touch sensing element can be used to sense if the electrode is contacted, e.g., through sensing the change of capacitance or resistance. Alternatively, it also can simply employ a switch to sense the force applied on the electrode. Accordingly, it can be further implemented that the electrocardiogram measurement starts automatically when the sensor or the switch senses a proper contacting force or other physical condition change applied on the electrode, such as, reaches a preset value, and even, it can be implemented that the device is initiated thereby.

Further, in the present invention, it is selective for the user to perform the blood pressure measurement, the ECG measurement or both. Here, it should be noted that the description of both measurements are performed means the two measurements are activated within a particular time period. That is, two measurements do not need to be started at the same time. For the present invention, the time period can be ranged from 0 to 10 minutes, and also, the two measurements can be overlapped or not. This time period is employed for providing more reasonable average physiological conditions of the user. Besides, two measurements can be implemented to be controlled by one processor or by multiple processors which should depend on the operation manner and the structure design without limitation.

In addition, other than the electrodes mounted on the housing and/or cuff, via an extension port, a connecting cable also can be employed to connect with other sensor/electrode, such as, an oximeter or a reference electrode, to expand the function.

In the aforesaid, the present invention provides a cardiovascular monitoring device with both functions of blood pressure measurement and electrocardiogram measurement and also a structure improvement in the blood pressure monitor for mounting the ECG electrode(s), so that the user can experience an easier, simpler and more convenient operation procedure. Moreover, the present invention also provides an ergonomic design for the user to contact the electrode(s) so as to ensure a more stable contact with the skin and thus a more accurate result. Furthermore, based on the correlation between the blood pressure and the electrocardiogram, the present invention can provide more useful indications for users' and doctors' reference.

The above examples and disclosures are intended to be illustrative and not exhaustive. These examples and descriptions will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is:
1. A cardiovascular monitoring device, comprising:
an inflatable cuff, for surrounding a limb of a user;
at least a first and a second electrodes, at least one of which is implemented as a dry electrode;
a housing;
a control circuitry with a processor, accommodated in the housing, wherein
the control circuitry is configured to perform a blood pressure measurement through controlling a pressure inside the cuff, and perform an electrocardiogram measurement by using the electrodes; and
the processor is configured to provide a diastolic blood pressure and a systolic blood pressure when the blood pressure measurement is performed, and to provide a heart rhythm information when the electrocardiogram measurement is performed; and
a display element, for showing the diastolic and systolic blood pressures and the heart rhythm information,
wherein
the device further comprises a force-receiving structure which is extended from the housing or the cuff and has the first and the second electrodes respectively positioned on opposite contactable surfaces thereof for achieving a simultaneous contact of the first and the second electrodes with different portions of the user's skin as a force is applied thereon.

2. The device as claimed in claim 1, wherein the first electrode and/or the second electrode is further connected to a sensor for detecting and/or notifying the contact thereon.

* * * * *